United States Patent [19]
Fujii et al.

[11] Patent Number: 6,060,254
[45] Date of Patent: May 9, 2000

[54] REAGENT FOR EXAMINING AGGLUTINATION OF VIRUS AND KIT FOR VIRUS EXAMINATION

[76] Inventors: Takeru Fujii, 446, Takashima Azaminami, Narutocho, Naruto-shi, Tokushima-ken, 772-0051; Hideakira Yokoyama, Excel Court Suehiro A-103, 1-12-5, Suehiro 5-chome, Tokushima-shi, Tokushima-ken, 770-0866; Hidetoshi Hamamoto, Yamaichikan 101, 27-2, Tarohachizu Azashinbori, Kitajima-cho, Itano-gun, Tokushima-ken, 771-0202, all of Japan

[21] Appl. No.: 09/011,748
[22] PCT Filed: Aug. 16, 1996
[86] PCT No.: PCT/JP96/02304
  § 371 Date: Apr. 21, 1998
  § 102(e) Date: Apr. 21, 1998
[87] PCT Pub. No.: WO97/07400
  PCT Pub. Date: Feb. 27, 1997

[30] Foreign Application Priority Data

Aug. 21, 1995 [JP] Japan .................................... 7-212221

[51] Int. Cl.[7] .............................. G01N 33/53; C12Q 1/70; C07K 1/00; C07K 16/00; C12P 21/08
[52] U.S. Cl. ................................ 435/7.1; 435/5; 435/810; 530/350; 530/388.35; 530/389.4; 530/391.1; 530/810
[58] Field of Search ................................ 435/5, 7.1, 810; 530/350, 388.35, 389.4, 391.1, 810

Primary Examiner—Hankyel Park
Assistant Examiner—Territa Gray
Attorney, Agent, or Firm—Oblon, Spivak, McClelland, Maier & Neustadt, P.C.

[57] ABSTRACT

A viral agglutination test agent and a virus test kit containing the agent, which can directly and sensitively detect viruses in blood without using the anti-viral antibody formed in the blood of patients with viral infections.

24 Claims, No Drawings

REAGENT FOR EXAMINING AGGLUTINATION OF VIRUS AND KIT FOR VIRUS EXAMINATION

TECHNICAL FIELD

This invention relates to a viral agglutination test agent and a virus test kit containing the said agent, which can detect sensitively and directly the viruses in blood without using the anti-viral antibody formed in blood of patients with viral infection. The viral agglutination test agent of the invention is useful for detection of all type of viruses, DNA virus or RNA virus, especially available for detection of viruses inducing continueous infections, such as hepatitis C virus (HCV), the main pathogen for non-A non-B hepatitis, and acquired immunodeficiency syndrome (AIDS) virus (HIV).

BACKGROUND ART

Among viral diseases, hepatitis C and AIDS, of which therapies have recently become a matter of serious concern, remain to be sufficiently clarified partly because the nature of the diseases had been kept unknown for a long time owing to the wide variation of the pathogenic viruses themselves. Therefore, the incidence of the secondary infection by these viruses was very high, and increase of patients could not effectively be suppressed. However the remarkable development in the gene-analytical technique in recent years has clarified the primary structure of the viruses in succession, so that the methods for detection of the viruses have been established at last and have eventually slowed down the spread of the secondary infection. It was found that in any of the above-mentioned viruses, the primary structure of the core protein is kept almost unvaried while the envelope protein is very variable. In addition, the progress in the gene technology has made it possible to mass-produce such proteins. In these circumstances, methods have been developed for detection of anti-viral antibodies formed in the serum of the patient, by using the envelope protein and also the core protein as the antigen, and these methods are now widely used in the routine examination.

However, these methods are problematic partly because they cannot make any definite statement as to the presence of infection for at least a few months, a period from the occurrence of viral infection until the formation of antibody within the virus-infected patient, so that they cannot effectively prevent the secondary infection, and partly because with these methods, diagnosis is difficult owing to false-negative results frequently obtained in patients with autoimmune diseases such as collagen disease. There is another problem that the test for the antibody alone cannot always draw a correct conclusion as to the presence of infection in a child infected by the mother-to-child route because he/she has the antibody inherited from his/her mother.

Additionally, RT-PCR method (reverse transcriptase-polymerase chain reaction method) to amplify its gene is used to detect RT (reverse transcriptase), which is relatively long maintained its primary structure consists in the viral agglutination test agent prepared by immobilizing molecules having affinity for the envelope protein of viruses onto the surface of solid microcarriers.

The viral agglutination test agent of the present invention is available for detecting DNA virus (Parvovirus, Papovavirus, Herpes virus, Hepatitis B virus (HBV), etc.,) and RNA virus [Paramyxovirus, Togavirus, Retrovirus (human immunodeficiency virus (HIV), Human T-lymphotropic virus (HTLV-1), etc.,), Hepatitis C virus (HCV), etc.,], especially available for detecting HIV and HCV.

Molecules having affinity for the viral envelope protein used in this invention are desirably proteins [monoclonal antibodies (anti-gp120 monoclonal antibody, anti-HCV monoclonal antibody, anti-HBV monoclonal antibody, anti-Herpes Simplex Virus I monoclonal antibody, anti-Herpes Simplex Virus II monoclonal antibody, anti-Varicella Zoster Virus II monoclonal antibody, anti-Cytomegalovirus monoclonal antibody, anti-Epstein-Barr Virus monoclonal antibody, anti-Measles Virus monoclonal antibody, and anti-HTLV-1 monoclonal antibody, etc.), polyclonal antibody, CD4, etc.] such as antibodies, or peptides (anti-gp120 polypeptide, etc).

The subject matter of the virus test kit of this invention consists in that the kit contains the above viral agglutination test agent and the positive control reagent. It is desirable that the kit contains the negative control reagent as well.

The positive control reagent is desirably the one prepared by immobilizing a part of or the whole of the viral envelop protein onto the surface of solid microcarriers, while the negative control reagent contains desirably a part of or the whole of the viral envelop protein.

BEST MODE FOR CARRYING OUT THE INVENTION

As the result of our researches to obtain a novel test agent which can directly detect the virus in serum and which can substitute the conventional antibody test methods, we found that a virus can directly be detected, in a short time, and sensitively by using agglutination of carriers labeled with molecules having affinity for a domain of the viral envelope protein present in the patient's blood, and we completed this invention. Therefore this invention includes ones, as far as molecules having affinity for the viral envelope protein are available, and carriers on which the said molecules are immobilized are available.

As mentioned above, the viral agglutination test agent of the invention is characterized in that molecules having affinity for the viral envelop protein are immobilized onto the surface of solid microcarriers. Hereinafter the solid microcarriers without the above-mentioned molecules having affinity for the protein are sometimes called, for convenience, unlabeled carriers, while the carrier with the molecules having affinity for the viral envelop protein (the carriers of this invention) are sometimes called molecules-labeled carriers.

The molecules having affinity for the viral envelope protein mean those which can recognize the envelope protein and be bound electrochemically or chemically to the said protein; such molecules are exemplified by soluble proteins such as polyclonal/monoclonal antibodies (anti-gp120 monoclonal antibody, anti-HCV monoclonal antibody, anti-HBV monoclonal antibody, anti-Herpes Simplex Virus I monoclonal antibody, anti-Herpes Simplex Virus II monoclonal antibody, anti-Varicella Zoster Virus II monoclonal antibody, anti-Cytomegalovirus monoclonal antibody, anti-Epstein-Barr Virus monoclonal antibody, anti-Measles Virus monoclonal antibody, and anti-HTLV-1 monoclonal antibody, etc.), CD4 (known as the binding sites for lymphocytes in HIV), etc. and polypeptides (anti-gp120 polypeptide, etc.). For the viruses, as defined in this invention, to which antibodies could hardly be prepared because of the wide variability, Tam et al. proposed a method for efficient preparation of antibodies which uses only the peptide in a specified domain as the antigen, and this method was applicable also to this invention (James P. Tam. In Synthetic Peptide: Approaches to Biological Problems, ed. J.

P. Tam and E. T. Kaiser, Multiple antigen peptide systems: A model design for synthetic peptide vaccine and immunoassay, pages 3–18, 1989, Alan R. Liss, Inc.).

The unlabeled carriers used in this invention are not specified as far as they are globular carrier used in usual agglutination methods such as latex, gelatin, polystyrene, colloidal gold, etc. The size of these carries may be selected from the range of 0.3 nm to 20 μm in diameter, and an optimal size can be selected according to the evaluation method of agglutination to be used. For example, for macroscopic evaluation of agglutination, it is desirable to employ carriers of 0.2 to 3 μm in diameter with which macroscopic judgment is easier, affinity for the viral envelop protein (the carriers of this invention) are sometimes called molecules-labeled carries.

The molecules having affinity for the viral envelop protein mean those which can recognize the envelop protein and be bound electrochemically or chemically to the said protein; such molecules are exemplified by soluble proteins such as polyclonal/monoclonal antibodies, CD4 (known as the binding sites for lymphocytes in HIV), etc. and polypeptides. For the viruses, as defined in this invention, to which antibodies could hardly be prepared because of the wide variability, Tam et al. proposed a method for efficient preparation of antibodies which uses only the peptide in a specified domain as the antigen, and this method was applicable also to this invention (James P. Tam. In Synthetic Peptide: Approaches to Biological Problems, ed. J. P. Tam and E. T. Kaiser, Multiple antigen peptide systems: A model design for synthetic peptide vaccine and immunoassay, pages 3–18, 1989, Alan R. Liss, Inc.)

The unlabeled carriers used in this invention are not specified as far as they are globular carries used in usual agglutination methods such as latex, gelatin, polystyrene, colloidal gold, etc. The size of these carriers may be selected from the range of 0.3 nm to 20 μm in diameter, and an optimal size can be selected according to the evaluation method of agglutination to be used. For example, for macroscopic evaluation of agglutination, it is desirable to employ carriers of 0.2 to 3 μm in diameter with which macroscopic judgment is easier, and for spectroscopic evaluation of agglutination, carriers of 0.2 μm or less in diameter may be used. The color of carriers is not restricted and is desirably selected according to the method of evaluation.

These unlabeled carriers may be dispersed in advance in a solution such as purified water, buffer, or serum, or lyophylized unlabeled carriers may be dissolved in a suitable solvent (e.g. purified water, buffer, etc.) before use.

The following is illustrated the method for detection of virus using the kit containing the above-mentioned viral agglutination test agent of this invention.

The virus test kit of this invention comprises, in addition to the above-mentioned viral agglutination test agent, a positive control reagent, and, if necessary, a negative control reagent.

The positive control reagent may be, as in the case of the usual antibody test method, the serum from a patient containing the target virus which has been made non-infective by heat treatment or chemical treatment and has been made usable for evaluation. Our researches found that it is more effective to use of a pseudo-virus model prepared by immobilizing a part of or the whole of the viral envelope protein onto the surface of the unlabeled carriers. Namely, the use of the pseudo-virus model is recommended from the viewpoint of the safety of handling during the test and the quality assurance of the positive control.

The negative control reagent may be selected among the serum from a normal subject having no target virus, buffer, salt-containing aqueous solution, a reagent containing the viral envelope protein, etc. From the viewpoint of quality assurance of the negative control in the kit of this invention, it is again recommended on a similar basis to use a reagent containing a part of or the whole of the viral envelope protein; in the concrete, the reagent may be dispersed in advance in a solvent such as purified water, buffer, or serum, or a lyophilized reagent may be dissolved before use in a suitable solvent (e.g. purified water, buffer, etc.).

As an example of the kit for virus test of the invention, the kit for HIV test is illustrated as to how to use it.

[HIV test kit]

Components (1) Anti-gp120-molecule-labeled latex reagent, 2 ml
(2) positive control [pseudo-HIV; gp120-labeled colloidal gold], 500 μl
(3) negative control [gp120], 500 μl
(4) agglutination plate, 20 plates
(5) diluted test sample, 50 ml How to use:

1. Before use, allow to stand the molecule-labeled latex reagent at room temperature until the normal temperature is reached. Before addition, mix carefully to avoid bubbles forming until a homogeneous suspension is obtained.

2. Add 20 μl of the molecule-labeled latex reagent into each well of the agglutination plate.

3. Add 20 μl each of the test sample, or the positive control/negative control, and mix well with the tip of a micropipet.

4. Rolling the agglutination plate for 1 to 2 minutes in hands.

5. Confirm that the agglutination is evidently recognizable with the positive control reagent, while no agglutination is obtained with the negative control reagent.

The virus agglutination test agent of the present invention is available for all type of viruses, DNA virus or RNA virus, especially available for detecting virus inducing continueous infections, such as DNA virus [Parvoviridae {Parvovirus (Kilham virus, etc.,)}, Papovaviridae {Papillomavirus (Shope pappilloma virus, etc.,), Polyomavirus (polyoma virus, etc.,),}, Herpesviridae {Herpes simplex virus I, Herpes simplex virus II, Varicella zostervirus, Cytomegalovirus, Epstein-Barr virus, etc.,}, Hepadnaviridae (HBV, etc.,) etc.,], RNA virus [Paramyxoviridae {Pneumovirus (Respiratory syncytial virus, etc.,), Paramyxovirus (Sendai virus, etc.,), Morbillivirus (Measles virus, etc.,), etc.,}, Togaviridae {Rubivirus (Rubella virus, etc.,), Flavivirus (Japanese encephalitis virus, etc.,), etc.,}, Retroviridae (HIV, HTLV-1 etc.,), Arenaviridae {Arenavirus (Lymphocytic choriomeningitis virus, etc.,) etc.,}, HCV, etc].

In the following, the invention is illustrated in more detail with the Preparations and Examples. However the Preparations and Examples described below do not limit the invention, and all variations, unless they deviate from the scope of the invention as described above or below, are included in the technical scope of the invention.

Preparation 1

To a suspension of activated latex beads (Polyscience Co., particle diameter: 0.2 μm), was added an equivalent amount of anti-gp120 monoclonal antibody (1 mg/ml of borate buffer, pH 8.3), and the mixture was allowed to react at 37° C. for 1 hour. After completion of the reaction, was added bovine serum albumin (10 mg/ml) so that its concentration became 0.1%, and blocking of the unreacted active groups was performed at room temperature for 30 minutes. Unreacted substances were removed by repeated centrifugation, and the buffer was substituted by the phosphate buffer (pH 7.4), to prepare HIV test agent.

The positive control was prepared by labeling colloidal gold of 0.3 μm in diameter (NanoProbe Co.) by the reaction with the recombinant gp120 expressed in vaculovirus. The negative control was prepared as a solution of the said recombinant gp120 in the phosphate buffer (pH 7.4).

Preparation 2

To the avidin-labeled latex beads (Molecular Probe Co.) suspension, was added an equivalent amount of biotinylated anti-NS(HCV) monoclonal antibody, and the mixture was allowed to react at 37° C. for 1 hour, to prepare HCV test agent. The positive and negative controls were colloidal gold preparations labeled with the recombinant NS and with human albumin, respectively. NS means non structure protein.

Preparation 3

Equivalent amounts of aldehyde-group-modified polystyrene beads (Interfacial Dynamics Co., particle diameter: 0.2 μm) and the anti-gp 120 monoclonal antibody (1 mg/ml of purified water) were mixed, to which triethylamine (10 mg/ml of purified water) was added to the concentration of 0.1%, and the mixture was allowed to react at room temperature for 1 hour, to prepare HIV test agent. Preparation of the positive control/the negative control was performed as described in the Preparation 1.

Preparation 4

Maleimidized colloidal gold (Molecular Probe Co., particle diameter: 3 nm) was allowed to react with the SH-group-introduced Fab' antibody prepared by using the anti-NS(HCV) monoclonal antibody, to prepare HCV test agent. Preparation of the positive negative control was performed as described in Preparation 2.

Preparation 5

Amino-group-modified latex beads (Interfacial Dynamics Co., particle diameter: 0.2 μm) were treated with glutaraldehyde, to which an equivalent amount of anti-gp120 monoclonal antibody (1 mg/ml of borate buffer, pH 8.3) was added, and the mixture was allowed to react. After completion of the reaction, the unreacted active groups were blocked with triethylamine, to prepare HIV test agent. Preparation of the positive control/negative control was performed as described in Preparation 1.

Preparation 6

To a suspension of activated latex beads (Polysciences Co., particle diameter: 0.2 μm), was added an equivalent amount of the recombinant CD4 (100 μg/ml of borate buffer, pH 8.3) expressed in vaculovirus, and the mixture was allowed to react at 37° C. for 1 hour, to prepare HIV test agent. Preparation of the positive control/negative control was performed as described in Preparation 1.

Preparation 7

To a suspension of colloidal gold (Polysciences Co., particle diameter: 0.03 μm), was added an equivalent amount of an anti-gp120 polypeptide solution, and the mixture was allowed to react at 37° C. for 1 hour, to prepare HIV test agent. Preparation of the positive control/negative control was performed as described in Preparation 1.

Preparation 8

To a suspension of activated latex beads (Polysciences Co., particle diameter: 0.2 μm), was added an equivalent amount of the NS (HCV) monoclonal antibody solution, and the mixture was allowed to react at 37° C. for 1 hour, to prepare HCV test agent. Preparation of the positive control/negative control was performed as described in Preparation 2.

Preparation 9

To a suspension of activated latex beads (Polysciences Co., particle diameter: 0.2 μm) was added an equivalent amount of the HBV monoclonal antibody, and the mixture was allowed to react at 37° C. for 1 hour, to prepare HBV test agent. The positive control and negative control were colloidal gold of 0.3 μm in diameter (NanoProbe Co.) preparations labeled with HBS antigen and human serum albumin, respectively.

Preparation 10

To a suspension of activated latex beads (Polysciences co., particle diameter: 0.2 μm), was added an equivalent amount of the anti-Herpes Simplex Virus I monoclonal antibody solution, and the mixture was allowed to react at 37° C. for 1 hour, to prepare Herpes Simplex Virus I. The positive control was prepared by labeling colloidal gold of 0.3 μm in diameter (NanoProbe Co.) by the reaction with partial purified Herpes Simplex Virus I cultured in Velo cell. The negative control was performed as described in Preparation 9.

Preparation 11

To a suspension of activated latex beads (Polysciences Co., particle diameter: 0.2 μm) was added an equivalent amount of the anti-Herpes Simplex Virus II monoclonal antibody, and the mixture was allowed to react at 37° C. for 1 hour, to prepare Herpes Simplex Virus II test agent. The positive control was prepared by labeling colloidal gold of 0.3 μm in diameter (NanoProbe Co.) by the reaction with partial purified Herpes Simplex Virus II cultured in Vero cell. The negative control was performed as described in Preparation 9.

Preparation 12

To a suspension of activated latex beads (Polysciences Co., particle diameter: 0.2 μm), was added an equivalent amount of the anti-Vaicella Zoster Virus monoclonal antibody, and the mixture was allowed to react at 37° C. for 1 hour, to prepare Vaicella Zoster Virus test agent. The positive control was prepared by labeling colloidal gold of 0.3 μm in diameter (NanoProbe Co.) by the reaction with partial purified Vaicella Zoster Virus cultured in human fibroblast cell. The negative control was performed as described in Preparation 9.

Preparation 13

To a suspension of activated latex beads (Polysciences Co., particle diameter: 0.2 μm) was added an equivalent amount of the anti-Cytomegalovirus monoclonal antibody, and the mixture was allowed to react at 37° C. for 1 hour, to prepare Cytomegalovirus test agent. The positive control was prepared by labeling colloidal gold of 0.3 μm in a diameter (NanoProbe Co.) by the reaction with partial purified Cytomegalovirus cultured in human fibroblast cell. The negative control was performed as described in Preparation 9.

Preparation 14

To a suspension of activated latex beads (Polysciences Co., particle diameter: 0.2 μm), was added an equivalent amount of the anti-Epstein-Barr virus monoclonal antibody, and the mixture was allowed to react at 37° C. for 1 hour, to prepare Epstein-Barr virus test agent. The positive control was prepared by labelling colloidal gold of 0.3 μm in diameter (NanoProbe Co.) by the reaction with partial purified Epstein-Barr virus from infectioned cells. The negative control was performed as described in Preparation 9.

Preparation 15

To a suspension of activated latex beads (Polysciences Co., particle diameter: 0.2 μm), was added an equivalent amount of the anti-Rubella Virus monoclonal antibody, and the mixture was allowed to react at 37° C. for 1 hour, to prepare Rubella Virus test agent. The positive control was prepared by labeling colloidal gold of 0.3 μm in diameter (NanoProbe Co.) by the reaction with partial purified Rubella Virus from infectioned cells cultured in Vero cell. The negative control was performed as described in Preparation 9.

Preparation 16

To a suspension of activated latex beads (Polysciences Co., particle diameter: 0.2 μm), was added an equivalent amount of the anti-HTLV-1 monoclonal antibody, and the mixture was allowed to react at 37° C. for 1 hour, to prepare HTLV-1 test agent. The positive control was prepared by labeling colloidal gold of 0.3 μm in diameter (NanoProbe Co.) by the reaction with partial purified HTLV-1 from infectioned cells. The negative control was performed as described in Preparation 9.

EXAMPLE 1

The sensitivity of the HIV test agent prepared as described in Preparation 7 was examined by using the HIV stock culture (HTLV-IIIB). The supernatant of this stock culture showed a negative result with the known HIV antibody test agent (CellodiaHIV, Fuji Rebio Co.). Before the examination, it was confirmed that the positive control described in Preparation 7 showed a positive result and the negative control showed a negative result, and also that the controls did not react at all to LAV-2, a HIV-2 type virus. Then the supernatant of the stock culture was diluted serially, and the resultant dilutions were allowed to react with the test agent of Preparation 7. The results are summarized in Table 1. The following tables 1–7 show that "+"/"−" means positive or negative, respectively.

TABLE 1

| HIV (dilution) | $10^1$ | $10^2$ | $10^3$ | $10^4$ | $10^5$ | $10^6$ | gp120/culture supernatant (negative control) |
|---|---|---|---|---|---|---|---|
| gp120/colloidal gold (positive control) 100 ug protein/ml | + | + | + | + | + | + | − |
| HTLV-IIIB (HIV-1) | + | + | + | + | + | − | − |

TABLE 1-continued

| HIV (dilution) | $10^1$ | $10^2$ | $10^3$ | $10^4$ | $10^5$ | $10^6$ | gp120/culture supernatant (negative control) |
|---|---|---|---|---|---|---|---|
| stock culture supernatant ($10^{4-5}$TCID$_{50}$/ml) | | | | | | | |
| LAV-2 (HIV-2) stock culture supernatant ($10^{4-5}$TCID$_{50}$/ml) | − | − | − | − | − | − | − |

As shown in Table 1, it was found that HIV test agent had good sensitivity of detection even at the dilution of $10^5$ fold. The limit of dilution-of-the HTLV-IIIB stock culture ($10^{4-5}$ TCID$_{50}$/ml) was $10^5$ fold, and this dilution fold was the limit at which the virus was supposed to be detected.

EXAMPLE 2

The HIV test agent of Preparation 7 was used to examine the sensitivity of the test agent with the 10-fold serial dilutions of HTLV-IIIB stock culture supernatant ($10^{4-5}$ TCID$_{50}$/ml) in inactivated human serum. The results are summarized in Table 2.

TABLE 2

| dilution in inactivated human serum | $10^1$ | $10^2$ | $10^3$ | $10^4$ | $10^5$ | $10^6$ |
|---|---|---|---|---|---|---|
| HTLV-IIIB ($10^{4-5}$TCID$_{50}$/ml) | + | + | + | + | − | − |

As shown in Table 2, it was found that HIV can be detected with the test agent of this invention without any influence on the sensitivity even when HIV was diluted 10,000 folds in human serum alone.

EXAMPLE 3

The HCV test agent of Preparation 8 was used to examine the sensitivity of the test agent with serum from various patients shown in Table 3. The results are summarized in Table 3.

TABLE 3

| | disease | | | | | |
|---|---|---|---|---|---|---|
| | hepatitis C | hepatitis B | AIDS | SLE* | progressive sclerema | sarcoidosis |
| HCV (Preparation 8) | + | − | − | − | − | − |

*SLE: systemic lupus erythematosus

As shown in Table 3, it was found that only hepatitis C can be specifically detected with the HCV test agent of this invention.

EXAMPLE 4

The HCV test agent of Preparation 9 was used to examine the sensibility of the test agent with serum from various patients shown in Table 4. The results are summarized in Table 4.

TABLE 4

|  | disease | | | |
| --- | --- | --- | --- | --- |
|  | hepatitis C | hepatitis B | SLE* | sarcoidosis |
| HCV (Preparation 9) | + | − | − | − |

*SLE: systemic lupus erythematosus

As shown in Table 4, it was found that only hepatitis B can be specifically detected with the HBV test agent of this invention.

EXAMPLE 5

The various virus test agent shown in Table 5 was used to examine the sensitivity of the test agent with serum from various positive control shown in Table 5. The results are summarized in Table 5.

TABLE 5

|  | Positive control | | | | |
| --- | --- | --- | --- | --- | --- |
| Test agent | Herpes Simplex Virus I | Herpes Simplex Virus II | Vaicella Zoster virus | Cytomegalo-virus | Epstein-Barr virus |
| Herpes Simplex Virus I (Preparation 10) | + | − | − | − | − |
| Herpes Simplex Virus II (Preparation 11) | − | + | − | − | − |
| Vaicella Zoster Virus (Preparation 12) | − | − | + | − | − |
| Cytomegalovirus (Preparation 13) | − | − | − | + | − |
| Epstein-Barr Virus (Preparation 14) | − | − | − | − | + |

As shown in table 5, it was found that only objective virus can be specifically detected with the test agent of this invention.

EXAMPLE 6

The various virus test agents shown in Table 6 were used to examine the sensibility of the test agent with serum from various positive control shown in Table 6. The results are summarized in Table 6.

TABLE 6

| Positive control | HIV | HIV | Rubella virus | HTLV-1 |
| --- | --- | --- | --- | --- |
| HIV (Preparation 1) | + | − | − | − |
| HCV (Preparation 8) | − | + | − | − |
| Rubella virus (Preparation 15) | − | − | + | − |
| HTLV-1 (Preparation 16) | − | − | − | + |

As shown in Table 6, it was found that only objective virus can be specifically detected with the test agent of this invention.

EXAMPLE 7

The various virus test agent shown in Table 7 was used to examine the sensitivity of the test agent with serum from various patients shown in Table 7. The results are summarized in Table 7.

TABLE 7

| Patients' serum | HIV | HBV | HCV | SLE | sarcoidosis |
| --- | --- | --- | --- | --- | --- |
| HIV (Preparation 7) | + | − | − | − | − |
| HBV (Preparation 8) | − | + | − | − | − |
| HCV (Preparation 9) | − | − | + | − | − |

As shown in Table 7, it was found that only objective virus can be specifically detected with the test agent of this invention.

[Industrial Applicability]

This invention has been constituted as described above, and shows following several advantages over the conventional antibody test methods.

(1) Because this invention directly detects viruses without using any antibody, the time lag (about 2 to 3 months) required for formation of an antibody in the patient's serum in the conventional antibody test methods is no more needed, so that the target virus can be detected immediately after viral infection.

(2) Viruses can sensitively be detected even in children infected through the mother-to-child route and in patients with autoimmune diseases such as collagen disease, where viruses were hardly detected with the conventional antibody test methods.

(3) Even an infectious viruses, which could not be detected with the conventional antibody test methods, can sensitively be detected.

(4) The conventional antibody test methods required the patient's serum containing the target virus as the positive control, whereas this invention uses solid microcarriers with the viral envelop protein immobilized on their surface. This invention is highly recommendable also from the viewpoint of assuring the safety on the examiner's side.

What is claimed is:

1. A viral agglutination test agent characterized in that molecules having affinity for the viral envelope protein are immobilized onto the surface of solid microcarriers.

2. A viral agglutination test agent as claimed in claim 1, wherein said viruses are DNA virus or RNA virus.

3. A viral agglutination test agent as claimed in claim 2, wherein said DNA virus is Parvovirus, Papovavirus, Herpes Virus or Hepatitis B virus.

4. A viral agglutination test agent as claimed in claim 2, wherein said RNA virus is Paramyxovirus, Togavirus, Retrovirus, or Hepatitis C Virus.

5. A viral agglutination test agent as claimed in claim 4, wherein said Retrovirus is Human Immunodeficiency Virus or Hum an T-Lymphotropic Virus.

6. A viral agglutination test agent as claimed in claim 1, wherein said molecules are protein or peptide.

7. A virus test kit characterized in that it contains the viral agglutination test agent as claimed in claim 1, and a positive control reagent.

8. A virus test kit as claimed in claim 7, wherein a negative control reagent is also contained.

9. A virus test kit as claimed in claim 7, wherein said positive control reagent is prepared by immobilizing a part of or the whole of the viral envelope protein onto solid microcarriers.

10. A virus test kit as claimed in claims 8, wherein said negative control reagent contains a part of or the whole of the viral envelope protein.

11. A viral agglutination test agent as claimed in claim 6, wherein said molecules are polyclonal antibody, monoclonal antibody, CD4, or polypeptide.

12. A viral agglutination test agent as claimed in claim 11, wherein said monoclonal antibody is selected from the group consisting of anti-HIV gp120 monoclonal antibody, anti-HCV monoclonal antibody, anti-HBV monoclonal antibody, anti-Herpes Simplex Virus I monoclonal antibody, anti-Herpes Simplex Virus II monoclonal antibody, anti-Varicella Zoster Virus II monoclonal antibody, anti-Cytomegalovirus monoclonal antibody, anti-Epstein-Barr Virus monoclonal antibody, anti-Measles Virus monoclonal antibody, and anti-HTLV-1 monoclonal antibody.

13. A viral agglutination test agent as claimed in claim 11, wherein said polypeptide is anti-HIV gp120 polypeptide.

14. A method of detecting a virus comprising:
   contacting a sample with a viral agglutination agent immobilized on a solid microcarrier,
   wherein the viral agglutination agent forms an agglutinate with the virus in the sample when the virus is present in the sample, and
   wherein the formation of the agglutinate is correlated with the presence of the virus in the sample, and the absence of the agglutinate is correlated with the absence of the virus in the sample.

15. The method of claim 14, wherein the solid microcarrier is gelatin.

16. The method of claim 14, wherein the solid microcarrier is latex beads.

17. The method of claim 14, wherein the solid microcarrier is polystyrene beads.

18. The method of claim 14, wherein the solid microcarrier is colloidal gold.

19. The method of claim 14, wherein the virus is a DNA virus.

20. The method of claim 14, wherein the virus is an RNA virus.

21. The method of claim 14, wherein the agglutination agent is a polyclonal antibody.

22. The method of claim 14, wherein the agglutination agent is a monoclonal antibody.

23. The method of claim 14, wherein the agglutination agent is CD4.

24. The method of claim 14, wherein the agglutination agent is a polypeptide.

* * * * *

UNITED STATES PATENT AND TRADEMARK OFFICE
CERTIFICATE OF CORRECTION

PATENT NO.    : 6,060,254                                          Page 1 of 1
DATED         : May 9, 2000
INVENTOR(S)   : Takeru Fujii et al.

It is certified that error appears in the above-identified patent and that said Letters Patent is hereby corrected as shown below:

Column 9,
Line 6, "C" should read -- B --.
Line 6, "B" should read -- C --.
Line 7, "HCV" should read -- HBV --.

Signed and Sealed this

Eighteenth Day of February, 2003

JAMES E. ROGAN
*Director of the United States Patent and Trademark Office*